United States Patent

Martin et al.

[11] Patent Number: 5,195,663
[45] Date of Patent: Mar. 23, 1993

[54] MIXING AND DISPENSING ASSEMBLY FOR PREPARATIONS SUCH AS DENTAL MATERIALS

[75] Inventors: Thomas W. Martin, Ramsey; Craig S. Hanson, Washington, both of Minn.

[73] Assignee: Minnesota Mining and Manufacturing Company, St. Paul, Minn.

[21] Appl. No.: 796,762

[22] Filed: Nov. 25, 1991

[51] Int. Cl.⁵ .............................................. B67D 5/42
[52] U.S. Cl. ................................... 222/327; 222/391
[58] Field of Search ............ 604/82, 92, 227, 232–235; 222/326, 327, 391

[56] References Cited

U.S. PATENT DOCUMENTS

| | | | |
|---|---|---|---|
| 1,704,678 | 3/1929 | Brown | 604/227 X |
| 2,193,489 | 3/1940 | Nevin | 604/92 |
| 3,348,545 | 10/1967 | Sarnoff | 222/327 X |
| 3,532,521 | 10/1970 | Bakan et al. | 106/35 |
| 3,572,337 | 12/1968 | Schunk | 604/227 X |
| 3,595,439 | 7/1971 | Newby et al. | 222/80 |
| 3,651,994 | 3/1972 | Nordenholt | 222/327 X |
| 3,684,136 | 8/1972 | Baumann | 222/386 |
| 3,739,947 | 6/1973 | Baumann et al. | 222/136 |
| 3,766,917 | 10/1973 | Wimmer | 128/218 M |
| 3,872,864 | 3/1975 | Allen, Jr. | 604/92 X |
| 3,933,961 | 1/1976 | Burns | 264/111 |
| 4,198,756 | 4/1980 | Dragan | 222/326 |
| 4,232,670 | 11/1980 | Richter et al. | 128/224 |
| 4,330,280 | 5/1982 | Dougherty et al. | 222/326 X |
| 4,391,590 | 7/1983 | Dougherty | 433/90 |
| 4,443,390 | 4/1984 | Brundige | 264/13 |
| 4,450,958 | 5/1984 | Prasad | 206/222 |
| 4,457,712 | 7/1984 | Dragan | 222/391 X |
| 4,636,198 | 1/1987 | Stade | 604/154 |
| 4,677,980 | 7/1987 | Reilly et al. | 128/655 |
| 4,737,151 | 4/1988 | Clement et al. | 222/327 X |
| 4,767,326 | 8/1988 | Bennett et al. | 433/90 |
| 4,972,969 | 11/1990 | Randklev | 222/1 |
| 5,026,283 | 6/1991 | Osanai et al. | 433/90 |

OTHER PUBLICATIONS

"The tableting of dental cement powders, J. T. Fell and E. C. Combe, *Journal of Dentistry,* " vol. 3, pp. 137–139 (1975).

"The effects of mixing capsule geometry on the early compressive strength of dental amalgam", Pearson and Atkinson, *Journal of Oral Rehabilitation,* vol. 15, pp. 347–352 (1988).

*Primary Examiner*—Andres Kashnikow
*Assistant Examiner*—Kenneth Bomberg
*Attorney, Agent, or Firm*—Gary L. Griswold; Walter N. Kirn; James D. Christoff

[57] ABSTRACT

A mixing and dispensing assembly includes a dispensing device having a receptacle. A capsule is removably received in the receptacle. The capsule has a single chamber and piston with a handle portion that is movable within the confines of the chamber. A tablet made of compacted powder is received in the chamber, and the piston is separated from the capsule when desired in order to add a liquid component and make the preparation.

4 Claims, 2 Drawing Sheets

MIXING AND DISPENSING ASSEMBLY FOR PREPARATIONS SUCH AS DENTAL MATERIALS

BACKGROUND OF THE INVENTION

1. Field of the Invention

This invention relates to a mixing and dispensing assembly that includes a single chamber capsule with a piston that is removable to add a liquid component.

2. Description of the Related Art

A number of mixing and dispensing capsules are known in the art, including capsules for storing, mixing and dispensing dental materials. Many capsules include two initially separate compartments that each hold one component of the desired, final preparation. Capsules for mixing and dispensing dental materials often have a configuration adapted to fit within a holding mechanism of a dental amalgamator that is operable to provide a vibratory motion to mix the components.

Some two-compartment mixing and dispensing capsules have a seal or membrane between the compartments that is ruptured to bring the components into contact with each other. The seal is ruptured either prior to a mixing operation or as a result of the vibratory motion presented by the amalgamator. An example of a mixing and dispensing capsule having a seal that is ruptured prior to the mixing operation is described in U.S. Pat. No. 3,595,439, assigned to the assignee of the present invention.

Certain capsules having two initially separate compartments are not entirely satisfactory, however, for all applications. For example, the liquid component of some preparations may tend to volatilize or diffuse through the seal over an extended period of time. Moreover, the user may desire in some instances to make a preparation having a ratio of the two components which is different from the ratio of the components as packaged.

U.S. Pat. No. 4,972,969, also assigned to the assignee of the present invention, describes a single chamber ampule that is initially provided with a single component, with an additional component or components added to the ampule immediately prior to use. The ampule is placed within a capsule, and the capsule is then secured in a holding mechanism of a dental amalgamator for mixing the ingredients. The ampule has flexible wall portions and may be compressed by finger pressure or by use of a dispenser in order to expel the mixed contents directly to an application site. While the ampule described in U.S. Pat. No. 4,972,969 is satisfactory for many applications, it is desirable in some instances to use a capsule having a piston that is movable upon movement of a lever actuated, ratchet-type dispensing device in order to utilize the mechanical advantage presented by a lever.

Occasionally, mixing of two or more components of a dental preparation is carried out by an end user by transferring the components from a bulk container to a relatively rigid capsule adapted for use with a conventional dental amalgamator. Measured quantities of each component are placed within the capsule, and the capsule is then closed and placed within an amalgamator to shake the capsule and mix the ingredients. Thereafter, a spatula or other device is utilized to remove the mixed contents from the capsule for transfer to the point of use. Such practice, however, necessitates careful cleaning and possibly sterilization of the capsule if the latter is to be re-used. Further, the mixture in the capsule cannot be conveniently applied to the application site without transfer to another tool or dispenser.

One disadvantage in working with preparations made of liquid and powder components is the possibility of displacing a portion of the powder component when the chamber of an amalgamator capsule is closed. For example, part of the powder component may "puff" and be displaced through the opening of the amalgamator capsule as it is closed. As can be understood, loss of a portion of the powder component may result in a preparation that does not have the desired physical or chemical properties.

SUMMARY OF THE INVENTION

The present invention is directed in one embodiment to an assembly for mixing and dispensing preparations and comprises a dispensing device having a housing with a receptacle, a lever movably connected to the housing, and a plunger connected to the lever. The plunger is movable toward the receptacle upon movement of the lever. The assembly also includes a mixing and dispensing capsule removably received in the receptacle. The capsule includes a chamber having an outlet and a piston movable in the chamber toward the outlet as the lever moves the plunger toward the receptacle. The piston is removable from the chamber and has a handle portion with a recess for gripping the piston. The handle portion is movable within the confines of the chamber.

In another embodiment, a mixing and dispensing capsule assembly according to the invention comprises a capsule having a chamber and an outlet next to the chamber. The capsule includes a piston having a head, a handle portion with a flange and a recess between the flange and the head for gripping the piston. The piston is removable by hand from the chamber for addition of a liquid component to the chamber. A tablet made of compacted powder is received in the chamber. The powder together with the liquid component comprise a preparation when mixed.

The present invention enables the end user to add a quantity of liquid component that may be varied to change physical or chemical properties of the preparation as desired. Dispensing of the mixed preparation from the chamber directly to an application site may be advantageously carried out by use of a commercially available, lever operated dispensing device.

DETAILED DESCRIPTION OF THE PREFERRED EMBODIMENTS

Figure 1:
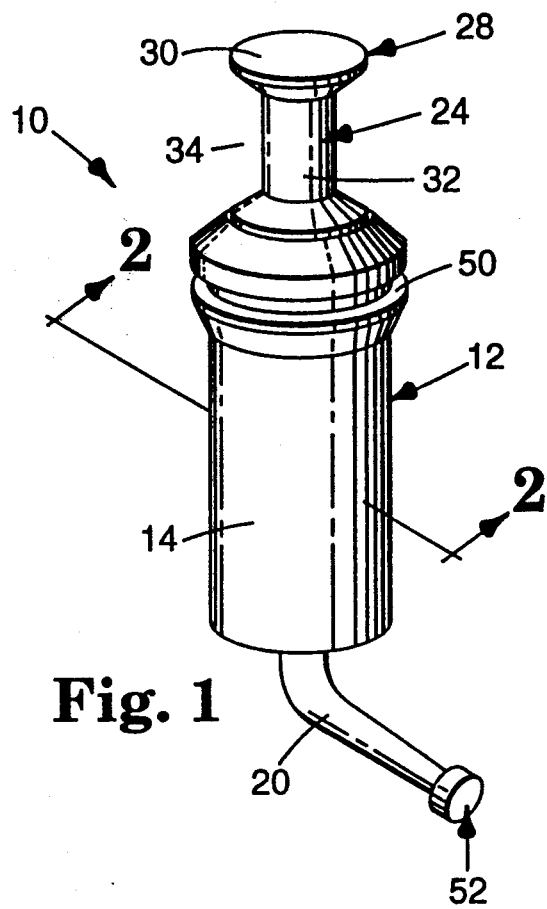
FIG. 1 is a perspective view of a mixing and dispensing capsule according to one embodiment of the invention.
Figure 2:
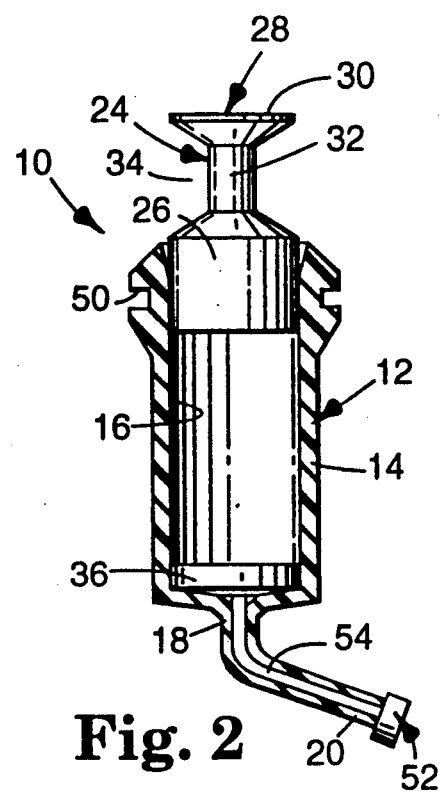
FIG. 2 is a side cross-sectional view taken along line 2—2 of FIG. 1.
Figure 3:
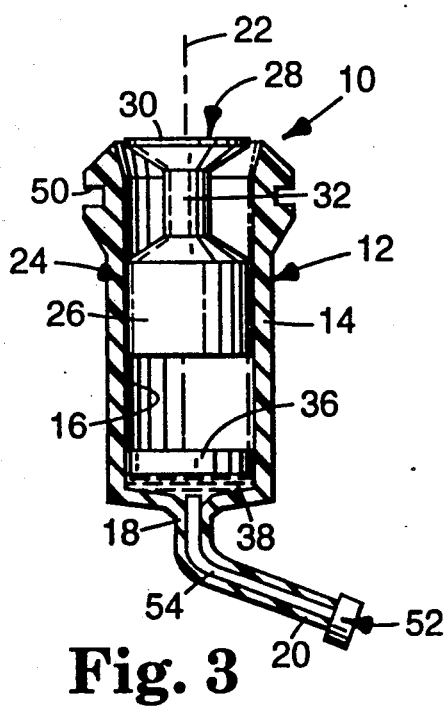
FIG. 3 is a view somewhat similar to FIG. 2 except that a liquid component has been added to a chamber of the capsule and the piston has been advanced in the chamber.

An assembly 10 for mixing and dispensing preparations such as dental materials includes a capsule 12 as illustrated in one embodiment in FIGS. 1–3. The capsule 12 includes a generally cylindrical body 14 having an internal cylindrical chamber 16 with a beveled entrance and an outlet 18 next to the chamber 16. The outlet 18 includes a slender tubular nozzle 20 having an angular configuration such that a front, outermost end of the nozzle 20 extends at a direction that is inclined relative to a central longitudinal axis 22 (FIG. 3) of the body 14.

The capsule 12 includes a piston 24 having a cylindrical head 26 and a handle portion 28. The handle portion 28 includes a frustoconical flange 30 and a narrowed, cylindrical stem 32 integrally interconnecting the flange 30 and the head 26. The flange 30 is spaced a sufficient distance from the head 26 to provide a recess 34 adjacent the stem 32 for gripping the piston 24 by the user's fingers when desired. As shown in FIGS. 1 and 2, the handle portion 28 including the recess 34 initially extend beyond the body 14.

The body 14 is made of a synthetic resinous material such as nylon, while the piston is preferably made of a different synthetic resinous material such as polypropylene. The diameter of the head 26 is at least equal to the diameter of the chamber 16, and preferably has a diameter that is slightly greater (e.g., 0.025 to 0.05 mm) than the diameter of the chamber 16 in order to provide an interference fit.

The piston 24 is removable from the chamber 16 by gripping the handle portion 28 and pulling the piston 24 in a direction away from the outlet 18. The interference fit between the piston head 26 and the chamber 16 is sufficient to retain the piston head 26 in the chamber 16 during expected shipping and handling and yet enable the piston head 26 to be removed by finger pressure from the chamber 16 when desired.

A tablet 36, as shown in FIGS. 2 and 3, is made of compacted powder and is received in the chamber 16. Once the piston 24 is separated from the body 14, a desired quantity of liquid component 38 is added to the chamber 16 as shown in FIG. 3. The liquid component 38 together with the powder of the tablet 36 comprise a preparation such as a dental material when mixed. An example of a preferred dental preparation is made from a glass powder and an ionomer liquid as described in European patent application No. 0 323 120.

FIG. 2 illustrates the position of the piston 24 as may be desirable, for example, when the capsule 12 is shipped to the end user and stored until use. After the piston 24 is separated from the body 14 by the end user and the liquid component 38 is added, the piston 24 is re-inserted in the chamber 16 and advanced toward the outlet 18 by pressing against the piston 24 with the user's thumb or fingers until the piston 24 reaches the position shown in FIG. 3.

Figure 5:
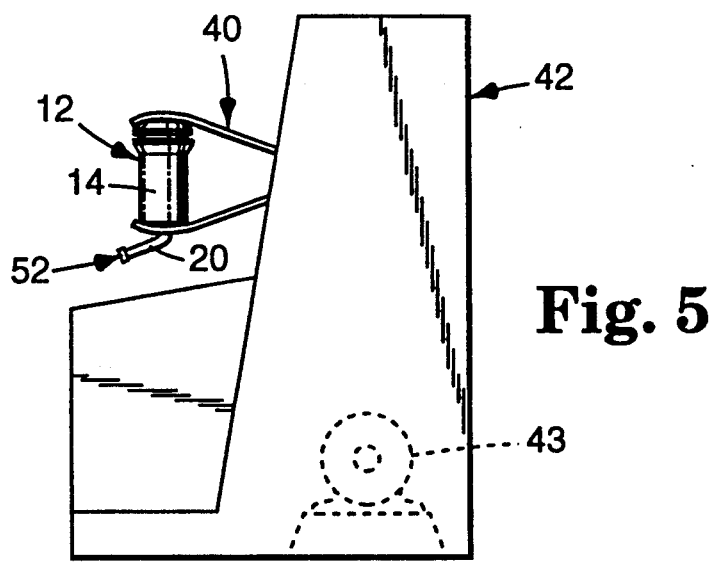
FIG. 5 is a reduced side view of the capsule shown in FIGS. 1-3 along with a dental amalgamator.

Next, the capsule 12 is placed in a holding mechanism 40 of a dental amalgamator 42 as illustrated in FIG. 5. The amalgamator 42 has a motor 43 that is then activated to move the capsule 12 in a rapid vibratory motion until such time as the tablet 36 has broken up and is essentially completely dissolved and thoroughly mixed with the liquid component 38.

Figure 6:
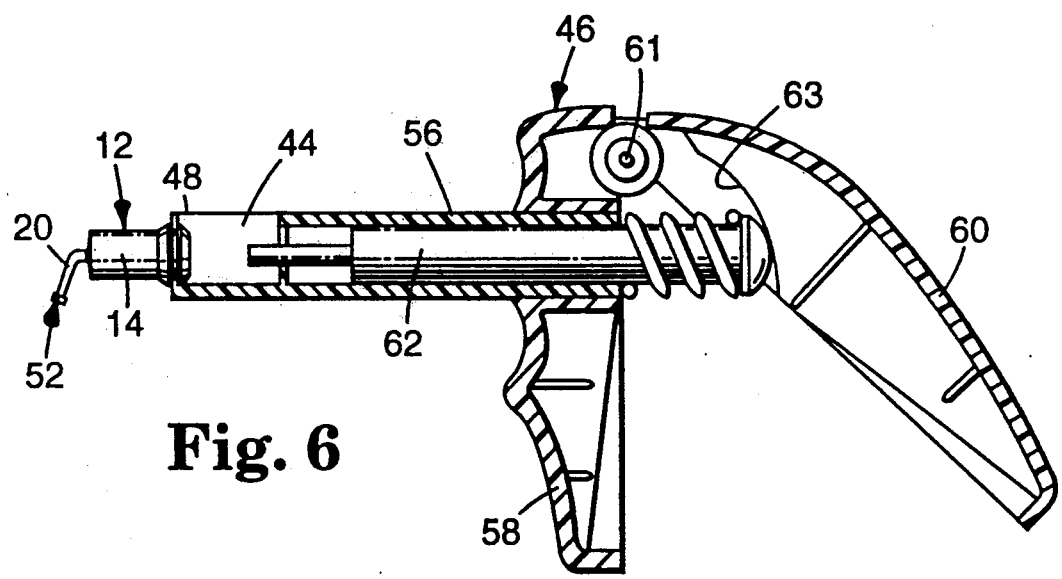
FIG. 6 is a cross-sectional view of a dispensing device along with a reduced side elevational view of the capsule shown in FIGS. 1-3.
Figure 7:
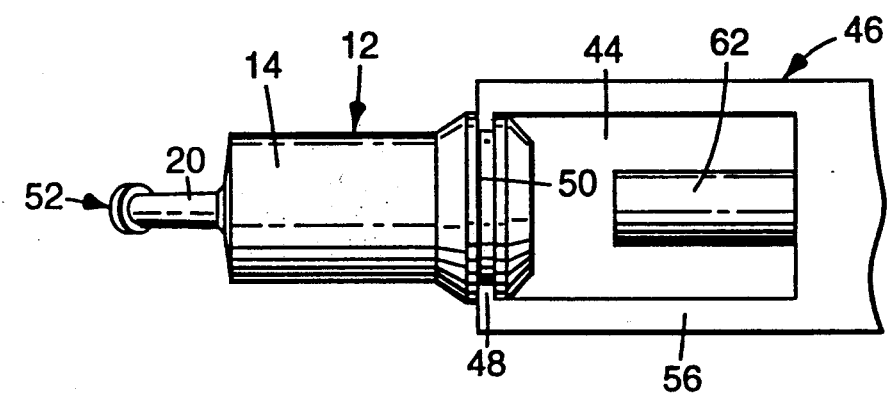
FIG. 7 is a fragmentary, enlarged plan view of the capsule and a portion of the dispenser shown in FIG. 6.

The capsule 12 is then removed from the holding mechanism 40 and placed in a receptacle 44 of a dispensing device 46 as shown in FIGS. 6 and 7. The receptacle includes a generally U-shaped retention wall 48 that is of a size adapted to fit into releasable, gripping engagement with a U-shaped groove 50 (see also FIGS. 1–3) that circumscribes a thickened rear portion of the capsule body 14.

Next, a plug 52 is removed from the capsule 12 to open the outlet 18. As illustrated in FIGS. 2 and 3, the plug 52 includes a tail 54 that preferably is flush with the forward end wall of the chamber 16 when the plug 52 is fully received in the nozzle 20.

The dispensing device 46 includes a housing 56 with a depending grip 58. A lever 60 is connected to the housing 56 by a pivot 61 and the lever 60 includes a cam surface 63 that is slidable against a rounded rearmost end of an elongated plunger 62. As the lever 60 is moved toward the grip 58, the plunger 62 shifts in a direction along its longitudinal axis toward the receptacle and contacts the rear end of the piston 24 of the capsule 12.

Figure 4:
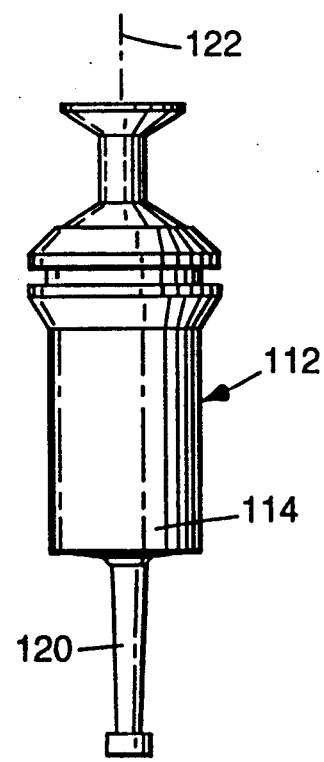
FIG. 4 is a side view of a capsule according to another embodiment of the invention.

Continued advancement of the lever 60 toward the grip 58 advances the piston 24 along the axis 22 and urges the mixed preparation from the chamber 16 and through the outlet 18 directly to an application site. The nozzle 20 shown in FIGS. 1–3 has an angular configuration for facilitating placement of the dispensed materials in certain instances. An alternate embodiment preferred in other instances is shown in FIG. 4, wherein a capsule 112 is essentially identical to the capsule 12 except that a nozzle 120 of the capsule 112 is straight and extends along a central, longitudinal axis 122 of a capsule body 114.

Advantageously, the flange 30 has an outer diameter that is equal to or smaller than the diameter of the piston head 26, so that the entire piston 24 can be received within the chamber 16 during a dispensing operation. As such, the capsule 12 may have an overall length sufficiently small to fit within the holding mechanism of conventional amalgamators such as amalgamator 42, and yet the chamber 16 of the capsule 12 has sufficient space for storing and mixing a variety of preparations for different uses. That is, the provision of the handle portion 28 that fits within the confines of the chamber 16 enables the use of a somewhat longer capsule 12 than would be possible if, for example, the piston handle could not fit within the confines of the chamber 16.

Preferably, the outer diameter of the flange 30 is equal to the diameter of the piston head 26, so that the flange 30 slidably engages the cylindrical wall defining the chamber 16 in order to enhance alignment of the piston 24 with the axis 22 as the mixed preparation is dispensed. In addition, the length of the piston head 26 in a direction along the axis 22 is great enough to provide stability and alignment of the piston head 26 to the axis 22. The piston 24 is movable to the forward end of the chamber 16 and thus is operable to expel substantially all of the preparation from the chamber 16.

The tablet 36 conveniently enables the piston 24 to be removed from the chamber 16 and then replaced in the chamber 16 without undue loss of the component as might be observed if, for example, the component were in the form of a powder. In addition, the tablet 36 provides a convenient "net weight" quantity of powder that may be readily placed in the chamber 16 by the manufacturer. While a selected quantity of powder component may be pressed into two or more tablets, a single tablet such as tablet 36 of proper quantity enables both the manufacturer and the end user to quickly ascertain that the desired quantity of powder component is present in the chamber 16.

The tablet 36 may have a disk-like configuration as shown, and alternatively may have an annular, pyramidal, cylindrical, spherical, rectangular, square or other configuration. The tablet is formed by placing an appropriate quantity of the powder component of the dental preparation in a form, and compressing with sufficient force to create a tablet with integrity. A process such as spray drying of the powder may be utilized to enhance the flowability of the powder to facilitate measuring of the powder for subsequent pressing in a compacting tablet press. Preferably, the tablet contains no binder or lubricant component that would deleteriously affect the properties of the ultimate preparation. For example, some additives are not desirable because they might have a potential dilution or interference effect on the ultimate preparation. Conversely, an additive that would maintain or enhance the ultimate properties of the preparation while at the same time serving a binder or lubricant function would be desirable. An example of such a component for use with dental materials might be a pyrogenic silica such as "OX 50" sold by Degussa.

The powder to liquid ratio may be varied by the end user in accordance with the desired physical or chemical properties of the preparation. For example, with dental glass ionomer materials made of two particular components, a core build-up preparation may be prepared by using a powder to liquid ratio of 2.5–3.0:1.0 (by weight), while a restorative material may be prepared by using a ratio of 2.0–2.4:1.0, and a luting cement, liner/base, sealant or adhesive preparation for orthodontic or endodontic application may be prepared by using a ratio of 1.2–1.6:1.0.

The present invention will be further understood in view of the following example which is merely illustrative and not meant to limit the scope of the invention. Unless otherwise indicated, all parts and percentages are by weight.

EXAMPLE

The ingredients set out below in TABLE I were mixed, melted in an arc furnace at about 1000°–1100° C., poured from the furnace in a thin stream and quenched using chilled rollers to provide an amorphous single-phase fluoroaluminosilicate glass:

TABLE I

| Ingredient | Parts |
|---|---|
| $SiO_2$ | 37 |
| $AlF_3$ | 23 |
| $SrO$ | 20 |
| $Al_2O_3$ | 10 |
| $Na_3AlF_6$ | 6 |
| $P_2O_5$ | 4 |

The glass was ball-milled to provide a pulverized frit with a surface area of 2.6–2.8 m²/g measured using the Brunauer, Emmet and Teller (BET) method.

A silanol treating solution was prepared by mixing 4 parts of gamma-methacryloxypropyl trimethoxysilane ("A-174", Union Carbide Corp.) and 55 parts water, and then acidifying with glacial acetic acid until the pH reached 2.7–2.9. The solution was stirred for 1 hour at room temperature. 100 Parts of the glass were combined with the silanol treating solution, slurried for 2 hours at room temperature, dried 4 hours at 45° C., and sieved through a 100 μm screen.

Disc-shaped tablets, each about 2.5 mm thick and about 10 mm in diameter and containing approximately 400 mg of the treated glass, were formed using a Courtoy press (Model No. R-100, AC Compacting Presses, Inc., North Brunswick, N.J.). Compression force settings of 600, 700, 900, 1100, 1200 and 1700 kg were independently used to form 5-6 tablets at each setting, with the press set to produce 200–400 tablets per minute. It was observed that the tablets formed at less than 900 kg could not be handled without breaking apart and tablets formed at 900 kg required gentle handling to remain intact. Tablets formed at 1100, 1200 and 1700 kg exhibited good integrity and ease of handling. However, tablets formed at compression forces of 1200 and 1700 kg could not be cleanly removed from the press without some tablet picking or delamination.

The piston was removed from a capsule similar to capsule 112 and a single tablet (or the equivalent of a single tablet) was placed in the capsule. A liquid prepared from the ingredients set out below in TABLE II was added to the tablet to form a dental preparation:

TABLE II

| Ingredient | Parts |
|---|---|
| Copolymer[1] | 53.0 |
| Water[2] | 28.2 |
| HEMA[3] | 18.8 |
| $(C_6H_5)_2I^+PF_6^-$ | 1.0 |
| CPQ[4] | 0.25 |
| BHT[5] | 0.05 |

[1]Ethylenically unsaturated acidic copolymer prepared like preparation of the precipitated dry polymer of EXAMPLE 11 of European Published Pat. Application No. 0 323 120.
[2]Distilled water.
[3]2-Hydroxyethyl methacrylate.
[4]Camphoroquinone.
[5]Butylated hydroxytoluene.

The ingredients were mixed using a blender (Twin Shell Dry Blender, Model No. LB-2033, Patterson-Kelley Company, Inc.) at room temperature (25° C.) under safelight conditions until a homogeneous solution was obtained. The solution was protected from exposure to ambient or artificial light by storage in an opaque container.

An amount of liquid was added to the tablet in the capsule to provide a powder to liquid ratio of 2.02–4:1.0. The piston was replaced and the capsule was placed in the holding mechanism of a Vivadent Silamat (Type S3) amalgamator and triturated for 10 seconds. The capsule was then removed from the amalgamator and placed in a dispensing device (GC Capsule Applier, G-C Dental Industrial Corp., Tokyo, Japan). The preparation was dispensed in a thin line onto a 0.05 mm thick sheet of clear polyester film. A second sheet of polyester film was placed on top of the preparation. The resultant sandwich was run across the edge of a desk top to form a very thin smear of the preparation. The sandwich was then held up to a fluorescent light and visually inspected for uniformity of the preparation.

Preparations made using tablets formed at 600, 700, 900 and 1100 kg provided uniformly mixed preparations with no visible agglomerates or undissolved powder in the resultant sandwich. However, preparations made using tablets formed at 1200 kg exhibited visible agglomerates in the sandwich, even when the trituration time was increased to 20 seconds. When tablets formed at 1700 kg were used to make preparations, the tablet remained essentially undissolved after a trituration time of 10 seconds, and numerous agglomerates were observed in the sandwich even after trituration time of 20 seconds.

We claim:

1. An assembly for mixing and dispensing preparations comprising:
   a dispensing device having a housing with a receptacle, a lever movably connected to the housing and a plunger connected to said lever, said plunger being movable toward said receptable upon movement of said lever; and
   a mixing and dispensing capsule removably received in said receptacle, said capsule including a chamber having an outlet and a piston movable in said chamber toward said outlet as said lever moves said plunger toward said receptacle, said piston being removable from said chamber and having a handle portion with a recess for gripping said piston, said handle portion being moveable within the confines of said chamber,
   wherein said piston includes a head having a certain diameter, and wherein said handle portion includes a flange having a diameter,
   wherein said diameter of said flange is equal to said certain diameter.

2. The assembly of claim 1, wherein said capsule includes a groove, and wherein said dispensing device includes a retention wall for engagement with said groove.

3. The assembly of claim 2, wherein said groove is of a size for friction-fit engagement with said retention wall.

4. The assembly of claim 1, and including a tablet received in said chamber, said tablet comprising a quantity of compacted powder material.

* * * * *

UNITED STATES PATENT AND TRADEMARK OFFICE
CERTIFICATE OF CORRECTION

PATENT NO. : 5,195,663

DATED : March 23, 1993

INVENTOR(S) : Thomas W. Martin and Craig S. Hanson

It is certified that error appears in the above-identified patent and that said Letters Patent is hereby corrected as shown below:

Col. 6, line 46, "2.02-4:1.0" should be -- 2.0-2.4:1.0 --.

Signed and Sealed this

Eleventh Day of January, 1994

Attest:

BRUCE LEHMAN

*Attesting Officer*       *Commissioner of Patents and Trademarks*